(12) United States Patent
Suriye et al.

(10) Patent No.: US 10,472,304 B2
(45) Date of Patent: Nov. 12, 2019

(54) CATALYST AND HYDROCARBON CONVERSION PROCESS UTILIZING THE CATALYST

(71) Applicant: SMH Co., Ltd, Bangkok (TH)

(72) Inventors: Kongkiat Suriye, Samutprakan (TH); Amnart Jantharasuk, Nakhon Si Thammarat (TH); Wuttithep Jareewatchara, Bangkok (TH)

(73) Assignee: SMH Co., Ltd, Bangkok (TH)

( * ) Notice: Subject to any disclaimer, the term of this patent is extended or adjusted under 35 U.S.C. 154(b) by 0 days.

(21) Appl. No.: 15/737,848

(22) PCT Filed: Jun. 29, 2016

(86) PCT No.: PCT/EP2016/065087
§ 371 (c)(1),
(2) Date: Dec. 19, 2017

(87) PCT Pub. No.: WO2017/001448
PCT Pub. Date: Jan. 5, 2017

(65) Prior Publication Data
US 2019/0002372 A1    Jan. 3, 2019

(30) Foreign Application Priority Data
Jun. 29, 2015  (EP) .................................. 15174327

(51) Int. Cl.
| | | |
|---|---|---|
| *C07C 5/333* | (2006.01) | |
| *B01J 37/04* | (2006.01) | |
| *B01J 23/652* | (2006.01) | |
| *C07C 6/10* | (2006.01) | |
| *B01J 37/18* | (2006.01) | |
| *B01J 38/12* | (2006.01) | |
| *B01J 23/00* | (2006.01) | |
| *B01J 23/28* | (2006.01) | |
| *B01J 23/30* | (2006.01) | |
| *B01J 23/36* | (2006.01) | |
| *B01J 23/656* | (2006.01) | |
| *B01J 23/92* | (2006.01) | |
| *B01J 23/96* | (2006.01) | |

(52) U.S. Cl.
CPC ........... *C07C 5/3337* (2013.01); *B01J 23/002* (2013.01); *B01J 23/28* (2013.01); *B01J 23/30* (2013.01); *B01J 23/36* (2013.01); *B01J 23/6525* (2013.01); *B01J 23/6527* (2013.01); *B01J 23/6567* (2013.01); *B01J 23/92* (2013.01); *B01J 23/96* (2013.01); *B01J 37/04* (2013.01); *B01J 37/18* (2013.01); *B01J 38/12* (2013.01); *C07C 6/10* (2013.01); *B01J 2523/00* (2013.01); *B01J 2523/13* (2013.01); *B01J 2523/31* (2013.01); *B01J 2523/36* (2013.01); *B01J 2523/3787* (2013.01); *B01J 2523/41* (2013.01); *B01J 2523/43* (2013.01); *B01J 2523/48* (2013.01); *B01J 2523/67* (2013.01); *B01J 2523/68* (2013.01); *B01J 2523/69* (2013.01); *B01J 2523/74* (2013.01); *B01J 2523/828* (2013.01); *C07C 2521/04* (2013.01); *C07C 2521/06* (2013.01); *C07C 2523/02* (2013.01); *C07C 2523/04* (2013.01); *C07C 2523/10* (2013.01); *C07C 2523/30* (2013.01); *C07C 2523/42* (2013.01); *C07C 2523/652* (2013.01); *C07C 2531/14* (2013.01); *Y02P 20/52* (2015.11); *Y02P 20/584* (2015.11)

(58) Field of Classification Search
CPC ..... C07C 5/3337; C07C 6/10; C07C 2523/02; C07C 2523/04; C07C 2523/10; C07C 2523/30; C07C 2523/42; C07C 2523/652; C07C 2521/04; C07C 2521/06; C07C 2531/14; B01J 23/002; B01J 23/28; B01J 23/30; B01J 23/36; B01J 23/6525; B01J 23/6567; B01J 23/92; B01J 23/96; B01J 38/12; B01J 37/04; B01J 37/18; B01J 23/6527; B01J 2523/3787; B01J 2523/00; B01J 2523/13; B01J 2523/31; B01J 2523/36; B01J 2523/41; B01J 2523/43; B01J 2523/48; B01J 2523/67; B01J 2523/68; B01J 2523/69; B01J 2523/828; Y02P 20/52; Y02P 20/584

See application file for complete search history.

(56) References Cited

U.S. PATENT DOCUMENTS

| | | |
|---|---|---|
| 3,932,548 A | 1/1976 | Rausch |
| 6,417,135 B1 | 7/2002 | Dyroff |

(Continued)

FOREIGN PATENT DOCUMENTS

EP      2689843 A1    1/2014

OTHER PUBLICATIONS

Sep. 15, 2016—International Search Report—PCT/EP2016/065087.

*Primary Examiner* — Brian A McCaig
*Assistant Examiner* — Jason Y Chong
(74) *Attorney, Agent, or Firm* — Banner & Witcoff, Ltd.

(57) ABSTRACT

The present invention relates to a hydrocarbon conversion catalyst comprising i) a catalyst, in oxidic form, metals M1, M2, M3 and M4, wherein: M1 is selected from Si, Al, Zr, and mixtures thereof; M2 is selected from Pt, Cr, and mixtures thereof; M3 is selected from W, Mo, Re and mixtures thereof; M4 is selected from Sn, K, Y, Yb and mixtures thereof; and ii) a hydrogen scavenger selected from at least one alkali and/or alkaline earth metal derivative, preferably in metallic, hydride, salt, complex or alloy form; as well as a hydrocarbon conversion process utilizing this catalyst.

21 Claims, No Drawings

(56) References Cited

U.S. PATENT DOCUMENTS

| | | | |
|---|---|---|---|
| 6,441,263 | B1 | 8/2002 | O'Rear et al. |
| 2004/0266612 | A1 | 12/2004 | Hayes et al. |
| 2009/0142258 | A1 | 6/2009 | Ritter et al. |
| 2014/0249339 | A1* | 9/2014 | Simanzhenkov .... B01J 19/0046 585/252 |

* cited by examiner

CATALYST AND HYDROCARBON CONVERSION PROCESS UTILIZING THE CATALYST

CROSS-REFERENCE TO RELATED APPLICATIONS

This application is a U.S. National Stage application under 35 U.S.C. § 371 of International Application PCT/EP2016/065087 (published as WO 2017/001448 A1), filed Jun. 29, 2016 which claims the benefit of priority to Application EP 15174327.5, filed Jun. 29, 2015. Benefit of the filing date of each of these prior applications is hereby claimed. Each of these prior applications is hereby incorporated by reference in its entirety.

The present invention relates to a hydrocarbon conversion catalyst and a process for conversion of a hydrocarbon feed comprising saturated hydrocarbon compounds to olefin products.

Olefins, especially light olefins including ethylene and propylene, are valuable hydrocarbon products. They are useful for preparing a wide variety of end products, including ethylene oxide, propylene oxide, ethyl benzene, acetone, phenol, polyethylene, polypropylene, other polymers, and other petrochemical products. Even though their prices have fluctuated over time, the demands in the industry have still been continuously growing.

To serve industrial needs, many methods have been used to produce olefins. However, it is typically more economically attractive to produce olefins from lower valued feedstock such as paraffins. A conventional method for converting saturated paraffins to olefins is thermal cracking. This is a highly energy intensive method and product selectivity is difficult to be adjusted and controlled.

Catalytic cracking is a later developed method. With appropriate catalytic materials, generally zeolite-based materials, hydrocarbon cracking can occur at less severe operating conditions.

In the art, also processes are known for converting saturated paraffins to olefins with a corresponding number of carbon atoms by dehydrogenation utilizing an appropriate catalyst. The dehydrogenation may be followed by an appropriate reaction step to further convert the obtained olefin into desired product(s). For example, the dehydrogenation may be followed by a metathesis step to convert the olefin obtained from the dehydrogenation step into different olefins.

Diverse side reactions may take place during dehydrogenation and the next reaction step, e.g. metathesis, for example the (re)hydrogenation of ethylene, propylene or butene which are preferred end products of a dehydrogenation reaction of ethane, propane or butane. In other words, the development of hydrogen may be a drawback in further reacting the obtained olefins.

It is therefore an object of the present invention to provide a hydrocarbon conversion catalyst and a respective process utilizing it wherein side reactions of hydrogen may be decreased or substantially prevented.

This object is achieved by a hydrocarbon conversion catalyst comprising i) a catalyst in oxidic form, comprising metals M1, M2, M3 and M4, wherein: M1 is selected from Si, Al, Zr, and mixtures thereof; M2 is selected from Pt, Cr, and mixtures thereof; M3 is selected from W, Mo, Re and mixtures thereof; M4 is selected from Sn, K, Y, Yb and mixtures thereof; wherein the mass fraction of M1 is in the range of 0.1 to 0.8; the mass fraction of M2 is in the range of 0.001 to 0.2; the mass fraction of M3 is in the range of 0.001 to 0.2; the mass fraction of M4 is in the range of 0.0001 to 0.2; and the mass fraction of oxygen is in the range of 0.1 to 0.8; and ii) a hydrogen scavenger selected from at least one alkali and/or alkaline earth metal derivative, preferably in metallic, hydride, salt, complex or alloy form.

According to the invention is also a process for conversion of a hydrocarbon feed comprising saturated hydrocarbon compounds to olefin products comprising contacting a hydrocarbon feed stream with the inventive hydrocarbon conversion catalyst.

Preferred embodiments are disclosed in the sub-claims.

In another embodiment of the present invention, the mass fraction of M1 is in the range of 0.2 to 0.6, the mass fraction of M2 is in the range of 0.0015 to 0.15, preferably 0.0015 to 0.05, the mass fraction of M3 is in the range of 0.005 to 0.15, preferably 0.01 to 0.1, and/or the mass fraction of M4 is in the range of 0.00015 to 0.03, preferably 0.0003 to 0.01. In another embodiment, the mass fraction of oxygen is in the range of 0.2 to 0.6.

In another embodiment, M2 is Pt and/or M3 is W.

In one embodiment, the process for conversion of the hydrocarbon feed of the present invention is carried out at a temperature in the range of 200-700° C., preferably 300-650° C., more preferably 400-600° C.

In another embodiment, the catalyst in oxidic form further comprises metal M5 (i.e. a catalyst of the formula M1M2M3M4M5O).

Preferably, M5 is selected from Mg, Ca, Mn, Fe, Co, Ni, Cu, and mixtures thereof; and the mass fraction of M5 is preferably in the range of 0.005 to 0.1, more preferably 0.005 to 0.05.

The mass fractions of M1-M4 and O, and of M1-M5 and O, respectively, sum up to 1 in the catalyst of the present invention.

In one embodiment, the at least one alkali and/or alkaline earth metal is selected from Li, Na, K, Mg, Ca, and mixtures thereof, preferably Na, and Mg.

It was surprisingly found that a hydrogen scavenger utilized in the inventive hydrocarbon conversion catalyst is capable of scavenging hydrogen in unwanted situations. The hydrogen scavenger selected for the present invention contains some hydrogen storage capacity. The hydrogen storage capability of the hydrogen scavenger can be either reversible or irreversible.

The catalyst in oxidic form can be prepared by mixing all precursors of the elements M1 to M4 or M1 to M5 together followed by a suitable heat treatment in order to obtain the desired multi-metal composition. Element precursors are starting compounds containing the desired elements which can be converted to the desired form of elements, preferably oxides, in the final catalyst by a suitable heat treatment. For example, precursor of M1 to M5 may include oxides, halides, alkoxides, nitrates, carbonates, formates, oxalates, amines, or hydroxides of the elements.

Mixing of element precursors can occur in dry form or wet form. When they are mixed in dry form, the element precursors may conveniently be provided in powder form. Powder of the element precursors can be easily mixed by physical mixing in a blender. The element precursors' mixture is then subjected to a suitable heat treatment, preferably calcination, to obtain the final catalyst in oxidic form. When they are mixed in wet form, the element precursors may be provided in solution and/or suspension form. A mixture of the element precursors' solutions and/or suspensions is then dried to remove the solvents. Subsequently, the dried mixture is subjected to a suitable heat treatment, preferably calcination, to obtain the final catalyst. Alternatively, and preferably, some of the element precursors may be provided in dry form and some of the element precursors may be provided in wet form. The dry and wet element precursors can be combined by conventional methods including impregnation, incipient wetness, ion-exchange, or other methods known in the art. The obtained mixture is then subjected to a suitable heat treatment, preferably calcination, to obtain the final catalyst. A suitable heat treatment involves a selected atmosphere and a selected temperature capable of removing and/or converting at least a part of the element precursors to the desired form of the corresponding elements in the final catalyst. Particularly preferred is that the elements are in oxidic form in the final catalyst. The selected atmosphere may include oxidizing atmosphere, reducing atmosphere, and inert atmosphere. In a preferred embodiment, the prepared catalyst powder is subjected to calcination in air at a temperature in the range of 300° C. to 800° C. for 1 to 24 hours, even more preferably 400° C. to 700° C. for 2 to 10 hours.

The catalyst in oxidic form can be also prepared by separately calcining one or more of the element precursors, then combining respective oxidic element precursors and finally calcining. For example, supports of zirconia, alumina, silica and/or zeolite (M1) are used to impregnate individually or simultaneously M2, M3 and M4 and/or M5 thereon. Respectively prepared individual compositions are then physically mixed and finally calcined. The hydrogen scavenger may be added to either of these mixtures or may be added when preparing the final mixture of all metals M1-M5 and the hydrogen scavenger.

In one preferred embodiment, the hydrocarbon conversion catalyst is prepared by physically mixing the catalyst in oxidic form, which is calcined and in a solid form, with the hydrogen scavenger, which is preferably also provided in solid form.

Suitably for the invention, the hydrogen scavenger is a derivative form of an alkali and/or alkaline earth metal, preferably metallic, hydride, salt, complex, alloy, or mixtures thereof.

The hydrogen scavenger is preferably prepared by subjecting a hydrogen scavenger precursor to an appropriate heat treatment, preferably calcination at a temperature in the range of 300° C. to 700° C., more preferably 400° C. to 600° C., for 2 to 24 hours.

The hydrogen scavenger precursor can be a compound of alkali and/or alkaline earth metal, preferably salt of an alkali and/or alkaline earth metal.

In an embodiment, the hydrogen scavenger precursor is selected from $Ca(BH_4)_2$, $Mg(BH_4)_2$, $Ca(NO_3)_2$, $K(NO_3)_2$, $Na(NO_3)_2$, and mixtures thereof.

It was found that at an appropriate heat treatment temperature and/or hydrocarbon conversion temperature, the hydrogen scavenger precursor is decomposed to be a derivative form of the alkali and/or alkaline earth metal. In this regard, in one embodiment of the present invention, the hydrogen scavenger is not present in oxidic form in the hydrocarbon conversion catalyst, but is present in a derivative form of alkali and/or alkaline earth metal, preferably metallic, hydride, salt, complex, alloy form or mixtures thereof.

In another embodiment, preparation of the hydrocarbon conversion catalyst according to the present invention may further involve forming the catalyst powder into a shape suitable for a commercial reactor. Shapes suitable for a commercial reactor may include pellets, extrudates, spheres, and the like. Sufficient binder materials may be further added to the catalyst composition to facilitate forming of the catalyst.

Contacting the hydrocarbon feed stream with the catalyst i) and the hydrogen scavenger ii) may occur separately or simultaneously. In a preferred embodiment, the catalyst i) and the hydrogen scavenger ii) are mixed, and contacting the hydrocarbon feed stream with the catalyst i) and the hydrogen scavenger ii) occurs simultaneously. Mixing of the catalyst i) and the hydrogen scavenger ii) may be performed in microscopic level or macroscopic level. In an embodiment, the hydrogen scavenger or its precursor is added to the preparation step of the catalyst i). Preferably, powders of the catalyst i) and the hydrogen scavenger ii) are physically mixed prior to contacting with the hydrocarbon feed stream. The powders mixture may be formed into a suitable shape, optionally with a suitable binder added, prior to contacting with the hydrocarbon feed stream. Also preferred is that the catalyst i) and the hydrogen scavenger ii) are physically mixed in a suitable weight ratio prior to contacting with the hydrocarbon feed stream. A suitable weight ratio of catalyst i) and hydrogen scavenger ii) in this regard may be from 1-99 to 99-1. A preferred weight ratio of catalyst i) to hydrogen scavenger ii) is in the range of 1-30 to 1, more preferably 2-25 to 1, even more preferably 4-20 to 1, even further more preferably 5-15 to 1.

In order to achieve olefins product, it is favorable that the hydrocarbon feed stream comprises a paraffinic hydrocarbon. In a preferred embodiment, the hydrocarbon feed stream comprises a paraffin having 2 to 5 carbon atoms. In a more specific embodiment, the hydrocarbon feed stream comprises a paraffin selected from ethane, propane, butane, pentane and mixtures thereof, preferably propane, butane, and a mixture thereof.

The hydrocarbon conversion process can be operated in a wide range of operating conditions. However, some specific ranges of operating conditions can result in high olefins production selectivity. In an embodiment, the process is carried out at a temperature in the range of 200° C. to 700° C., preferably 300° C. to 650° C., even more preferably 400° C. to 600° C. In another embodiment, the process is carried out at a pressure in the range of 0.01 to 10 bar gauge, preferably 0.05 to 5 bar gauge. The contact time needed to obtain a desirable yield of olefins product depends upon several factors such as operating temperature, operating pressure, and catalyst activity. In an embodiment, the process is carried out at a weight hourly space velocity (WHSV) in the range of 0.01 to 20 $hr^{-1}$, preferably 0.05 to 5 $hr^{-1}$. The process can be conducted in a batch manner or a continuous manner. For commercial scale, it is favorable that the process is continuously operated. Continuous operation can be performed with fixed bed, fluidized bed, or other techniques known in the art with fixed bed being typically preferred.

Prior to contacting with the hydrocarbon feed stream, the catalyst i) and the hydrogen scavenger ii) may optionally be pretreated. The pretreatment condition may include contacting the catalyst i) and the hydrogen scavenger ii) with an inert gas, an oxidizing gas, a reducing gas, a hydrocarbon, preferably a C2-C6 aliphatic hydrocarbon, and any mixture thereof. The pretreatment may be divided into several steps wherein each step may employ different conditions and atmospheres. It is generally preferred that the pretreatment is performed at a heated temperature, preferably 200° C. to 700° C., more preferably 300° C. to 600° C., even more preferably 350° C. to 550° C.

After contact with the hydrocarbon feed stream at the operating condition, some poisonous substances, heavy hydrocarbons, and coke may deposit on the surface of the catalyst and the hydrogen scavenger. This normally affects activity of the catalyst mixture to gradually drop over time. A suitable regeneration can be performed on the used mixture of the catalyst and hydrogen scavenger to recover at least some of its activity. In an embodiment, the hydrocarbon conversion process comprises a regeneration step wherein the regeneration step includes contacting the hydrocarbon conversion catalyst with an oxidizing agent at a high temperature. The regeneration step should be carefully controlled to avoid overheating and destroying structure of the catalyst. In an embodiment, the regeneration step is carried out at a temperature in the range of 200° C. to 700° C., preferably 300° C. to 600° C. Other known regeneration techniques can be employed without limitation.

A variety of hydrocarbon conversion catalysts according to the invention have been prepared and tested according to the above disclosure. It was surprisingly found by the inventors that catalyst systems (of inventive catalyst and inventive hydrogen scavenger) falling within the scope of the claims featured better catalytic activity and selectivity in comparison to non-inventive catalyst systems.

Furthermore, it was surprisingly found that the catalyst systems according to the invention can be operated under mild conditions, i.e. at temperatures significantly lower than known in the art.

EXPERIMENTAL RESULTS

In the examples section below, the conversion of propane into olefins, preferably ethylene and butene, has been investigated using hydrocarbon conversion catalysts according to the present invention and comparative catalysts.

Example A

Each example catalyst was pretreated by contacting with air at approximately 500° C. for 30 minutes and with hydrogen at approximately 500° C. for 90 minutes before contacted with C3H8 at approximately 500° C., 0.1 bar gauge, and WHSV of 0.2 $h^{-1}$. The results were measured at time on stream for approximately 60-65 hours. Effluents from the reaction were directed to a gas chromatography apparatus to measure their chemical composition. The measured compositions of effluents were used to calculate conversion and selectivity. Percent C3H8 conversion was calculated from the weight of C3H8 converted during reaction divided by weight of C3H8 in feed stream and then multiplied by 100. Percent selectivity of each other product was calculated also from the weight of that specific product produced from the reaction divided by weight of all products produced from the reaction and then multiplied by 100. The composition of catalyst was calculated from the amount of precursor used to prepare the catalyst. The mass fraction can be calculated from the weight percentage divided by 100.

| | | Result | | | | | | | | |
|---|---|---|---|---|---|---|---|---|---|---|
| | | C3H8 | | Selectivity (% wt) | | | | | | |
| Example | Catalyst (% wt) | Conversion (% wt) | Total Olefins | CH4 | C2H4 | C2H6 | C3H6 | C4H8 | C4H10 | C5+ |
| 1 (compare) | 0.811 Al<br>1.792 Mg<br>50.495 O<br>0.501 Pt<br>42.526 Si<br>3.396 W<br>0.076 Yb<br>0.403 Zr | 10.858 | 77.279 | 6.038 | 8.505 | 14.252 | 54.499 | 13.243 | 2.429 | 1.032 |
| 2 (compare) | 0.649 Al<br>6.977 B<br>3.903 H<br>1.433 Mg<br>9.040 N<br>40.438 O<br>0.401 Pt<br>34.058 Si<br>2.716 W<br>0.061 Yb<br>0.323 Zr | 10.481 | 86.695 | 4.854 | 2.902 | 6.837 | 78.846 | 4.946 | 0.907 | 0 |
| 3 (inventive) | 0.649 Al<br>1.433 Mg<br>3.283 N<br>5.388 Na<br>51.687 O<br>0.401 Pt<br>34.058 Si<br>2.716 W<br>0.061 Yb<br>0.323 Zr | 11.451 | 84.668 | 4.172 | 9.877 | 8.216 | 53.427 | 19.648 | 1.075 | 1.715 |
| 4 (inventive) | 0.725 Al<br>1.600 Mg<br>1.800 N<br>2.955 Na<br>51.143 O<br>0.445 Pt<br>37.873 Si<br>3.032 W<br>0.068 Yb<br>0.358 Zr | 14.783 | 79.676 | 6.146 | 9.675 | 12.457 | 53.146 | 15.526 | 1.716 | 1.327 |

-continued

| | | Result | | | | | | | | |
|---|---|---|---|---|---|---|---|---|---|---|
| | | C3H8 | | Selectivity (% wt) | | | | | | |
| Example | Catalyst (% wt) | Conversion (% wt) | Total Olefins | CH4 | C2H4 | C2H6 | C3H6 | C4H8 | C4H10 | C5+ |
| 5 (inventive) | 0.722 Al 4.306 K 1.594 Mg 1.543 N 50.156 O 0.444 Pt 37.787 Si 3.021 W 0.068 Yb 0.358 Zr | 10.695 | 84.389 | 5.830 | 9.803 | 8.688 | 59.617 | 13.965 | 1.091 | 1.003 |

Example 1 (Comparative)

A catalyst sample containing 0.811 wt % of Al, 1.792 wt % of Mg, 50.495 wt % of O, 0.501 wt % of Pt, 42.526 wt % of Si, 3.396 wt % of W, 0.076 wt % of Yb, and 0.403 wt % Zr was calcined at 550° C. for 3 hours in air before subjected to the reaction test.

This catalyst is a standard catalyst for conversion of paraffins into olefins without adding hydrogen scavenger.

Example 2 (Comparative)

The catalyst sample was prepared by:
1) Providing a powder catalyst containing 0.810 wt % of Al, 1.789 wt % of Mg, 50.497 wt % of O, 0.5 wt % of Pt, 42.53 wt % of Si, 3.391 wt % of W, 0.076 wt % of Yb, and 0.403 wt % of Zr.
2) Calcining the powder catalyst in step 1) at 550° C. for 3 hours in air.
3) Calcining NH3BH3 at 550° C. for 3 hours in air.
4) Physically mixing 80 wt % of the calcined catalyst from step 2) with 20 wt % of calcined NH3BH3 from step 3).

Using of this catalyst shows higher olefins selectivity, however it seems NH3BH3 suppressed metathesis activity of W and therefore ethylene and butylene selectivity were significantly lowered.

Example 3

The catalyst sample was prepared by:
1) Providing a powder catalyst containing 0.811 wt % of Al, 1.791 wt % of Mg, 50.448 wt % of O, 0.501 wt % of Pt, 42.573 wt % of Si, 3.395 wt % of W, 0.076 wt % of Yb, and 0.403 wt % of Zr.
2) Calcining the powder catalyst in step 1) at 550° C. for 3 hours in air.
3) Calcining Na(NO3) at 550° C. for 3 hours in air.
4) Physically mixing 80 wt % of the calcined catalyst from step 2) with 20 wt % of calcined Na(NO3) from step 3).

Use of this catalyst can suppress hydrogenation side reaction. This is evidenced by higher C2H4 and C4H8 selectivity but lower C2H6 and C4H10 selectivity compared to the standard catalyst in Example 1.

Example 4

The catalyst sample was prepared by the same steps as Example 3, but 10 wt % of Na(NO3) was used.

Use of this catalyst can suppress hydrogenation side reaction. This is evidenced by higher C2H4 and C4H8 selectivity but lower C2H6 and C4H10 selectivity compared to the standard catalyst in Example 1.

Example 5

The catalyst sample was prepared by the same steps as the Example 3, but 10 wt % of K(NO3) was used instead of Na(NO3).

Use of this catalyst can suppress hydrogenation side reaction. This is evidenced by higher C2H4 and C4H8 selectivity but lower C2H6 and C4H10 selectivity compared to the standard catalyst in Example 1.

Example B

Each example catalyst was pretreated by contacting with air at approximately 500° C. for 30 minutes and with hydrogen at approximately 500° C. for 90 minutes before contacted with C3H8 at approximately 550° C., 0.05-0.1 bar gauge, and WHSV of approximately 0.4-0.7 h-1. The results were measured at time on stream approximately 155-160 hours.

| | | Result | | | | | | | | |
|---|---|---|---|---|---|---|---|---|---|---|
| | | C3H8 | | Selectivity (% wt) | | | | | | |
| Example | Catalyst (% wt) | Conversion (% wt) | Total Olefins | CH4 | C2H4 | C2H6 | C3H6 | C4H8 | C4H10 | C5+ |
| 6 (compare) | 0.324 Al 0.715 Mg 49.624 O 4.277 Pt 42.700 Si 1.355 W | 27.719 | 75.199 | 1.519 | 6.934 | 17.655 | 44.806 | 20.063 | 3.512 | 3.394 |

-continued

| Example | Catalyst (% wt) | C3H8 Conversion (% wt) | Total Olefins | CH4 | C2H4 | C2H6 | C3H6 | C4H8 | C4H10 | C5+ |
|---|---|---|---|---|---|---|---|---|---|---|
| 7 (inventive) | 0.390 Yb<br>0.641 Zr<br>0.649 Al<br>6.093 B<br>11.294 Ca<br>2.272 H<br>1.432 Mg<br>39.375 O<br>2.159 Pt<br>33.131 Si<br>2.715 W | 24.276 | 93.554 | 1.311 | 8.276 | 3.353 | 69.419 | 14.841 | 0.722 | 1.016 |
| 8 (inventive) | 0.574 Yb<br>0.307 Zr<br>0.753 Al<br>2.518 B<br>0.939 H<br>4.492 Mg<br>45.930 O<br>2.531 Pt<br>38.654 Si<br>3.151 W<br>0.673 Yb<br>0.360 Zr | 27.504 | 86.788 | 1.874 | 14.874 | 7.912 | 46.881 | 20.795 | 1.474 | 4.402 |

Example 6 (Comparative)

A catalyst sample containing 0.324 wt % of Al, 0.715 wt % of Mg, 49.624 wt % of O, 4.277 wt % of Pt, 42.700 wt % of Si, 1.355 wt % of W, 0.390 wt % of Yb, 0.641 wt % Zr was calcined at 550° C. for 3 hours in air before subjected to the reaction test.

Example 7

The catalyst sample was prepared by:

1) Providing a powder catalyst containing 0.801 wt % of Al, 1.782 wt % of Mg, 49.009 wt % of O, 2.687 wt % of Pt, 41.237 wt % of Si, 3.379 wt % of W, 0.714 wt % of Yb, and 0.382 wt % of Zr.

2) Calcining the powder catalyst in step 1) at 550° C. for 3 hours in air.

3) Calcining $Ca(BH_4)_2$ at 550° C. for 3 hours in air.

4) Physically mixing 80 wt % of the calcined catalyst from step 2) with 20 wt % of calcined Ca(BH4)2 from step 3).

Use of this catalyst can suppress hydrogenation side reaction. This is evidenced by lower C2H6 and C4H10 selectivity compared to the standard catalyst in Example 6.

Example 8

The catalyst sample was prepared by the same steps as the Example 7, but 6.5 wt % of Mg(BH4)2 was used instead of Ca(BH4)2.

Use of this catalyst can suppress hydrogenation side reaction. This is evidenced by lower C2H6 and C4H10 selectivity compared to the standard catalyst in Example 6.

The features disclosed in the foregoing description and in the claims may, both separately and in any combination thereof, be material for realizing the invention in diverse forms.

The invention claimed is:

1. A process for conversion of a hydrocarbon feed comprising saturated hydrocarbon compounds to olefin products comprising contacting the hydrocarbon feed with a hydrocarbon conversion catalyst comprising:
    i) metals M1, M2, M3 and M4, wherein:
        M1 is selected from Si, Al, Zr, and mixtures thereof;
        M2 is selected from Pt, Cr, and mixtures thereof;
        M3 is W;
        M4 is selected from Sn, K, Y, Yb, and mixtures thereof
        wherein
        a mass fraction of M1 is in the range of 0.1 to 0.8;
        a mass fraction of M2 is in the range of 0.001 to 0.2;
        a mass fraction of M3 is in the range of 0.001 to 0.2;
        a mass fraction of M4 is in the range of 0.0001 to 0.2; and
        a mass fraction of oxygen is in the range of 0.1 to 0.8; and
    ii) at least one alkali metal and/or alkaline earth metal in a metallic, hydride, salt, complex, or alloy form.

2. The process of claim 1, wherein the at least one alkali metal and/or alkaline earth metal is selected from Li, Na, K, Mg, Ca, and mixtures thereof.

3. The process of claim 2, wherein the at least one alkali metal and/or alkaline earth metal is Na or Mg.

4. The process of claim 1, wherein a weight ratio of catalyst i) said metals M1, M2, M3 and M14 and ii) said alkali metal and/or alkaline earth metal, is from 1-99 to 99-1.

5. The process of claim 1, wherein M2 is Pt and M3 is W.

6. The process according to claim 1, wherein the hydrocarbon feed comprises at least one paraffin having 2 to 5 carbon atoms.

7. The process of claim 6, wherein the hydrocarbon feed comprises propane, n-butane, or a mixture thereof.

8. The process of claim 7, wherein the hydrocarbon feed comprises propane and wherein the olefin products comprise ethylene and butene, resulting from the conversion of the propane.

9. The process according to claim 1, additionally comprising a regeneration step of the hydrocarbon conversion catalyst comprising heating the hydrocarbon conversion catalyst with an oxidizing agent at a temperature of about 200-700° C.

10. The process according to claim 9, wherein the oxidizing agent comprises air or oxygen.

11. The process of claim 1, wherein said metals M1, M2, M3, and M4 are in oxide forms.

12. The process of claim 1, wherein the catalyst further comprises metal M5 in oxide form, wherein M5 is selected from the group consisting of Mg, Ca, Mn, Fe, Co, Ni, Cu, and mixtures thereof.

13. The process of claim 12, wherein said metal M1 is in oxide form, and further wherein said oxide form of M1 and said oxide form of M5 are obtained by heat treatment of corresponding precursor forms of M1 and M5, said corresponding precursor forms independently selected from the group consisting of a halide form, an alkoxide form, a nitrate form, a carbonate form, a formate form, an oxalate form, an amine form, and a hydroxide form.

14. The process of claim 13, wherein said corresponding precursor forms are independently selected from the group consisting of the carbonate form and the hydroxide form.

15. A process for conversion of a hydrocarbon feed comprising saturated hydrocarbon compounds to olefin products comprising contacting the hydrocarbon feed with a hydrocarbon conversion catalyst comprising:
   i) metals M1, M2, M3 and M4, wherein:
      M1 is selected from Si, Al, Zr, and mixtures thereof;
      M2 is selected from Pt, Cr, and mixtures thereof;
      M3 is W;
      M4 is selected from Sn, K, Y, Yb, and mixtures thereof
      wherein
      a mass fraction of M1 is in the range of 0.1 to 0.8;
      a mass fraction of M2 is in the range of 0.001 to 0.2;
      a mass fraction of M3 is in the range of 0.001 to 0.2;
      a mass fraction of M4 is in the range of 0.0001 to 0.2; and
      a mass fraction of oxygen is in the range of 0.1 to 0.8; and
   ii) at least one alkali metal and/or alkaline earth metal selected from the group consisting of Li, Na, Mg, Ca, and mixtures thereof,
      wherein the hydrocarbon feed comprises propane and wherein the olefin products comprise ethylene and butene, resulting from the conversion of the propane.

16. The process of claim 15, wherein said metals M1, M2, M3, and M4 are in oxide forms.

17. The process of claim 15, wherein said catalyst further comprises metal M5 in an oxide form, wherein M5 is selected from the group consisting of Mg, Ca, Mn, Fe, Co, Ni, Cu, and mixtures thereof.

18. The process of claim 17, wherein said metal M1 is in oxide form, and further wherein said oxide form of M1 and said oxide form of M5 are obtained by heat treatment of corresponding precursor forms of M1 and M5, said corresponding precursor forms independently selected from the group consisting of a halide form, an alkoxide form, a nitrate form, a carbonate form, a formate form, an oxalate form, an amine form, and a hydroxide form.

19. A process for conversion of a hydrocarbon feed comprising saturated hydrocarbon compounds to olefin products comprising contacting the hydrocarbon feed with a hydrocarbon conversion catalyst comprising:
   i) metals M1, M2, M3, and M4, wherein:
      said metals M1, M2, M3, and M4 are in oxide forms;
      M1 is selected from Si, Al, Zr, and mixtures thereof;
      M2 is selected from Pt, Cr, and mixtures thereof;
      M3 is selected from W, Mo, Re and mixtures thereof;
      M4 is selected from Sn, K, Y, Yb, and mixtures thereof;
      wherein
      a mass fraction of M1 is in the range of 0.1 to 0.8;
      a mass fraction of M2 is in the range of 0.001 to 0.2;
      a mass fraction of M3 is in the range of 0.001 to 0.2;
      a mass fraction of M4 is in the range of 0.0001 to 0.2; and
      a mass fraction of oxygen is in the range of 0.1 to 0.8; and
   ii) at least one alkali metal and/or alkaline earth metal selected from the group consisting of Li, Na, Mg, Ca, and mixtures thereof,
      wherein the hydrocarbon feed comprises propane and wherein the olefin products comprise ethylene and butene, resulting from conversion of the propane.

20. The process of claim 19, wherein said catalyst further comprises metal M5 in an oxide form, wherein M5 is selected from the group consisting of Mg, Ca, Mn, Fe, Co, Ni, Cu, and mixtures thereof.

21. The process of claim 20, wherein said metal M1 is in oxide form, and further wherein said oxide form of M1 and said oxide form of M5 are obtained by heat treatment of corresponding precursor forms of M1 and M5, said corresponding precursor forms independently selected from the group consisting of a halide form, an alkoxide form, a nitrate form, a carbonate form, a formate form, an oxalate form, an amine form, and a hydroxide form.

* * * * *